United States Patent [19]

Pease

[11] Patent Number: 4,538,463
[45] Date of Patent: Sep. 3, 1985

[54] FLAW DETECTION IN WIRE DRAWING

[75] Inventor: Nicolas C. Pease, Bishop Stortford, England

[73] Assignee: International Standard Electric Corporation, New York, N.Y.

[21] Appl. No.: 589,971

[22] Filed: Mar. 15, 1984

[30] Foreign Application Priority Data

Mar. 16, 1983 [GB] United Kingdom ............ 8307242

[51] Int. Cl.³ .............................................. G01N 29/04
[52] U.S. Cl. ........................................................ 73/587
[58] Field of Search .................................. 73/587, 104

[56] References Cited

U.S. PATENT DOCUMENTS 4,487,068 12/1984 Hawkins ............................... 73/587

Primary Examiner—Anthony V. Ciarlante
Attorney, Agent, or Firm—John T. O'Halloran; Peter R. Ruzek

[57] ABSTRACT

A method of detecting the presence of flaws in wire as it passes through a wire drawing die involves monitoring the output in the megacycle range of an acoustic sensor attached to the drawing die.

9 Claims, 1 Drawing Figure

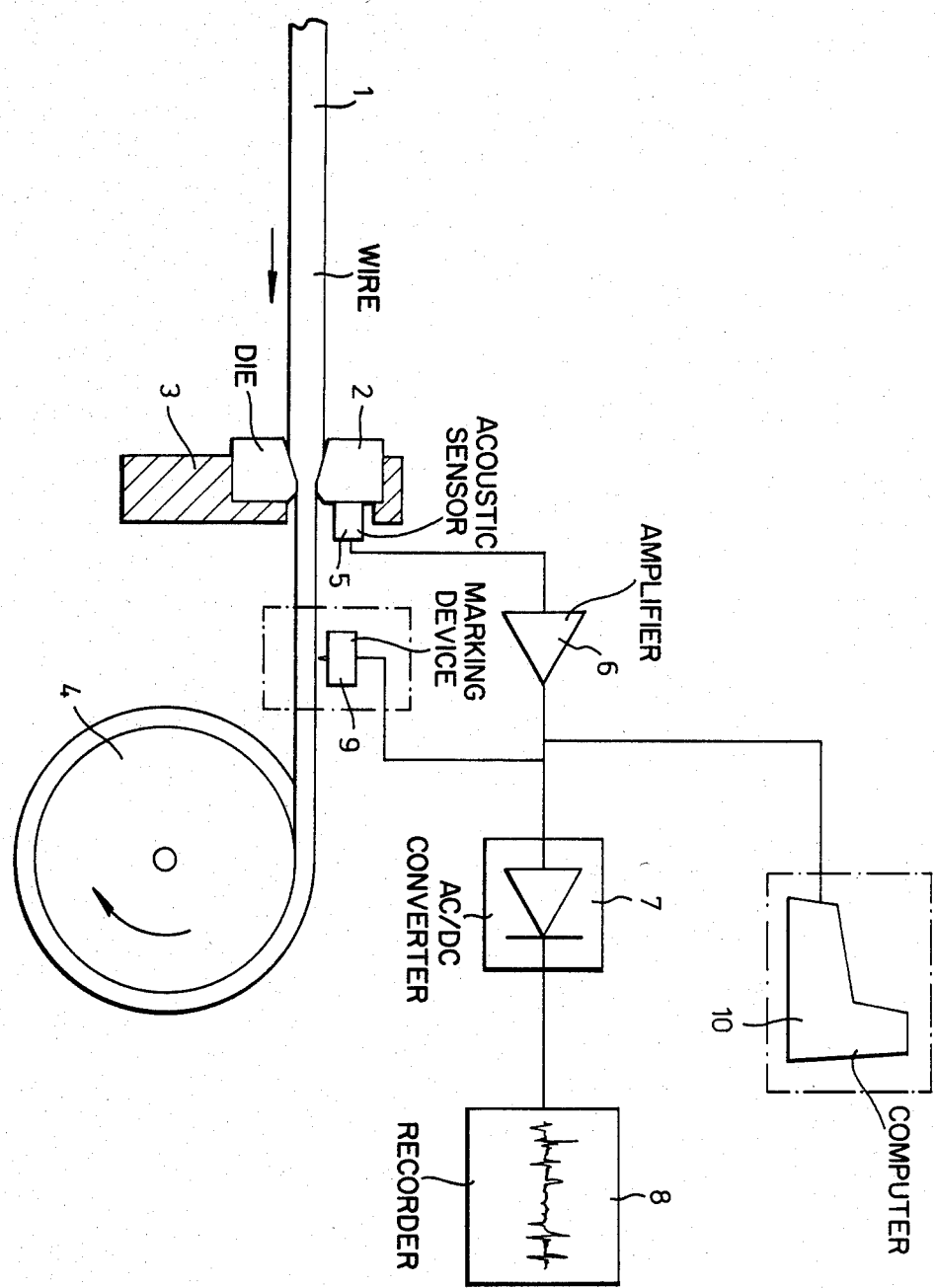

FLAW DETECTION IN WIRE DRAWING

BACKGROUND OF THE INVENTION

The present invention relates to the detection of flaws in wire as that wire passes through a drawing die.

A paper by T. Sato et al entitled 'Assessment of Frictional Conditions by Acoustic-Emission Technique in Metal Forming' appearing in the Journal of the Japanese Society for Technology of Plasticity 21 (1980) 608–613 refers to laboratory experiments on the monitoring of acoustic emission during sheet-and wire-drawing of aluminum, and concludes that this approach has potential for detecting changes in the frictional conditions at the die/wire interface resulting from interruption in the supply of lubricant or wear of the die. Two types of sensors were used, one having a resonance frequency of 23 kHz and characteristic in the range 200 Hz to 15 kHz, and the other having a resonance frequency of 300 kHz. However, this approach is suited only for detecting the aforementioned changes and does not give discernible information about any physical properties of the wire being drawn. Yet, experience has shown that the wire, or a section thereof, may be useless by including a flaw that goes undetected when the above monitoring is used.

SUMMARY OF THE INVENTION

Accordingly, it is a general object of the present invention to avoid the disadvantages of the prior art.

More particularly, it is an object of the present invention to provide a method of detecting flaws in a wire being drawn through a die.

Still another object of the present invention is to develop a method of the above kind which would be simple to perform and achieve reliable results.

A concomitant object of the present invention is to devise an apparatus for performing the method of the type here under consideration, which would be relatively simple in construction, inexpensive to manufacture, easy to use, and reliable in operation nevertheless.

According to the present invention there is provided a method of detecting the presence of flaws in wire as it passes through a wire drawing die in which an acoustic sensor having a response in the megacycle range is secured to the die and the sensor output is monitored for transient events. Thus, the present invention involves monitoring acoustic emission at significantly higher frequencies than before, that is, in the megacycle range. Quite surprisingly, this approach results in the appearance of pronounced temporary deviations in the sensor output signal as irregular, especially cracked or otherwise faulty, portions of the wire pass through the die so that, to detect such faults, it is merely necessary to search for "short-time" events, which will occur as blips or bursts of energy superimposed on background noise energy characteristic of die wear or lubricant starvation.

BRIEF DESCRIPTION OF THE DRAWING

There follows a description of apparatus embodying the invention in a preferred form for detecting the presence of flaws in wire as that wire is passed through a drawing die, with reference to a sole figure of accompanying drawing which is a schematic representation of the apparatus from performing the present invention.

DETAILED DESCRIPTION OF THE PREFERRED EMBODIMENT

Referring now to the drawing in detail, it may be seen that a length of wire 1 is being drawn through a wire drawing die 2 by a capstan 4. The die 2 is supported in a dieholder 3, and the die 2, the die-holder 3 and the capstan 4 may form part of a standard commercial wire-drawing machine, with the proviso that the die-holder 3 may require minor modification to accommodate an acoustic sensor 5 which is attached to the surface of the die 2 via a suitable fluid coupling medium. The sensor 5 is so constructed in a manner that is well known in the art, as to give response to acoustic waves predominantly if not exclusively in the megacycle range.

The output signal of the sensor 5 is fed to an amplifier 6 from which it may then proceed to an AC/DC converter 7 after which it is fed to a chart recorder 8. The chart recorder 8 provides a recorded trace representative of the output of the sensor 5. Passage of a faulty portion of the wire 1 through the die 2 will appear as a significant temporary deviation from the usual behavior of the trace, thus providing an indication of such a fault. Optionally the signal from the amplifier 6 is fed to a marking device 9 which marks the wire 1 at the point where a potential flaw is detected so that later that portion of the wire 1 may be readily identified for further examination. The signal from the amplifier 6 may also be digitized and fed to a computer 10 for spectral and/or amplitude analysis to give information on the type and severity of the fault encountered.

While we have described above the principles of our invention in connection with specific apparatus, it is to be clearly understood that this description is made only by way of example and not as a limitation to the scope of our invention as set forth in the objects thereof and in the accompanying claims.

I claim:

1. A method of detecting the presence of flaws in a wire as it passes through a wire drawing die, comprising the steps of
    sensing acoustic waves issued during the passage of the wire through the die, at least in the megacycle range, and generating an electrical signal representative of such acoustic waves; and
    monitoring the electrical signal for the occurrence of transient events therein.

2. The method as defined in claim 1, wherein said monitoring step includes providing a visual display of the behavior of the electrical signal.

3. The method as defined in claim 1, wherein said monitoring step includes analyzing the behavior of the electrical signal in a data processor.

4. The method as defined in claim 1, and further comprising the step of marking the section of the wire affected by the flaw in accordance with the results of said monitoring step.

5. An apparatus for detecting the presence of flaws in a wire as it passes through a wire drawing die, comprising
    an acoustic sensor operative for sensing acoustic waves issued during the passage of the wire through the die, at least in the megacycle range, and operative for generating an electrical signal representative of such acoustic waves; and
    means for monitoring said electrical signal for the presence of transient events therein.

6. The apparatus as defined in claim 5, wherein said acoustic sensor is affixed to said die.

7. The apparatus as defined in claim 5, wherein said monitoring means includes means for providing a visual display of the behavior of the electrical signal.

8. The apparatus as defined in claim 5, wherein said monitoring means includes means for analyzing the behavior of the electrical signal, including data processing means.

9. The apparatus as defined in claim 5, and further comprising means for marking the section of the wire affected by the flaw in accordance with the output of said monitoring means.

* * * * *